(12) United States Patent
Maki

(10) Patent No.: US 9,351,811 B2
(45) Date of Patent: May 31, 2016

(54) ORTHODONTIC BRACKET

(75) Inventor: Koutaro Maki, Tokyo (JP)

(73) Assignee: GC Corporation, Tokyo (JP)

( * ) Notice: Subject to any disclaimer, the term of this patent is extended or adjusted under 35 U.S.C. 154(b) by 419 days.

(21) Appl. No.: 13/258,290

(22) PCT Filed: Apr. 14, 2010

(86) PCT No.: PCT/JP2010/056645
§ 371 (c)(1),
(2), (4) Date: Sep. 21, 2011

(87) PCT Pub. No.: WO2010/119880
PCT Pub. Date: Oct. 21, 2010

(65) Prior Publication Data
US 2012/0009538 A1    Jan. 12, 2012

(30) Foreign Application Priority Data

Apr. 16, 2009 (JP) .................. 2009-099754

(51) Int. Cl.
*A61C 7/14* (2006.01)
*A61C 7/16* (2006.01)
*A61C 7/28* (2006.01)

(52) U.S. Cl.
CPC . *A61C 7/14* (2013.01); *A61C 7/143* (2013.01); *A61C 7/16* (2013.01); *A61C 7/28* (2013.01); *A61C 7/282* (2013.01)

(58) Field of Classification Search
CPC ............ A61C 7/12; A61C 7/14; A61C 7/143; A61C 7/16; A61C 7/28; A61C 7/282
USPC ................. 433/8, 9, 10, 16, 17, 18, 24
See application file for complete search history.

(56) References Cited

U.S. PATENT DOCUMENTS

| 4,184,254 | A | | 1/1980 | Kraus |
| 5,022,854 | A | | 6/1991 | Broughton et al. |
| 5,358,402 | A | | 10/1994 | Reed et al. |
| 5,474,444 | A | * | 12/1995 | Wildman .................... 433/8 |
| 6,347,939 | B2 | * | 2/2002 | Abels ......................... 433/10 |
| 6,733,286 | B2 | | 5/2004 | Abels et al. |

(Continued)

FOREIGN PATENT DOCUMENTS

DE    2616767    12/1977
DE    9308153.7 U1    7/1993

(Continued)

*Primary Examiner* — Cris L Rodriguez
*Assistant Examiner* — Hao D Mai
(74) *Attorney, Agent, or Firm* — The Webb Law Firm

(57) ABSTRACT

Provided is an orthodontic bracket that is capable of a more effective motion on the tooth surface. The orthodontic bracket includes a substrate surface that is bonded to the tooth surface and an arch wire retaining portion that is configured to retain an arch wire with the substrate surface as a bottom surface, the orthodontic bracket being connected by the arch wire and continuously applying a stress to individual teeth to thereby straighten a row of teeth, wherein the orthodontic bracket is in an approximately cambered cross-sectional shape that is orthogonal to the direction in which the arch wire is stretched with the substrate surface bonded to the tooth surface as the bottom surface, and is provided with a plurality of arch wire through holes respectively for inserting the arch wires into the holes and connecting adjacent orthodontic brackets by the arch wires.

14 Claims, 11 Drawing Sheets

(56) References Cited

U.S. PATENT DOCUMENTS

| | | |
|---|---|---|
| 7,396,230 B2 * | 7/2008 | Abels et al. ............... 433/11 |
| 2007/0015103 A1 | 1/2007 | Sorel |
| 2007/0031773 A1 * | 2/2007 | Scuzzo ...................... 433/10 |
| 2008/0081310 A1 * | 4/2008 | Smith et al. ............... 433/17 |
| 2008/0213718 A1 * | 9/2008 | Abels et al. ............... 433/8 |
| 2009/0035715 A1 * | 2/2009 | Cleary ....................... 433/19 |

FOREIGN PATENT DOCUMENTS

| | | |
|---|---|---|
| EP | 1226791 A1 | 7/2002 |
| JP | 2001161716 A | 6/2001 |
| JP | 2005502388 A | 1/2005 |
| JP | 2007105361 A | 4/2007 |
| JP | 2007522852 A | 8/2007 |
| WO | 02065939 A1 | 8/2002 |

* cited by examiner

ORTHODONTIC BRACKET

TECHNICAL FIELD

The present invention relates to an orthodontic bracket.

BACKGROUND ART

A good alignment of the teeth creates a favorable impression on the social life and makes an excellent force of mastication from a point of medical view. Consequently, a lot of people have an orthodontic treatment in recent years. In particular, a force of mastication has been reduced for modern people in accordance with a variation of a food culture. Therefore, a space for growing the teeth in a mouth of modern people has a tendency to be decreased, and an alignment of the teeth has a tendency to be degraded for modern people in the case in which an orthodontic treatment is not carried out.

Based on the above tendency, an orthodontic treatment is carried out in a childhood when permanent teeth are grown in many cases.

For an orthodontic treatment in general, an orientation of a tooth is tried to be modified by a series of operations described in the following as disclosed in Japanese Patent Application Laid-Open Publication No. 2001-161716 for instance (see FIG. 10 and FIG. 11 herein).
(1) An orthodontic bracket 143 is bonded to a surface 141A of a plurality of teeth.
(2) An arch wire 146 is fitted by insertion to a depressed part 145 that has been formed in the bracket 143, and the arch wire 146 is disposed across between the brackets 143.
(3) An elastic force of the arch wire 146 is applied to the teeth.

Such an orthodontic bracket 143 has been made of a metal. Consequently, the orthodontic bracket 143 is not so aesthetic due to a difference between the color tones of a tooth and a metal bracket. In order to improve the problem point, a transparent plastic or a plastic that is tinctured to be a color similar to a color tone of a tooth is used as a constitutional material of the orthodontic bracket 143.

However, the orthodontic bracket and the arch wire are engaged with each other only by fitting the arch wire by insertion to the depressed part 145 that has been formed in the orthodontic bracket. Consequently, in order to fit the arch wire to the orthodontic bracket that is disposed at the end part, it has been general that the orthodontic bracket that is disposed at the end part and the arch wire are tied up by using a wire 150 for a ligation. In addition, since the arch wire 146 is fitted by insertion to the depressed part 145 that has been formed in the bracket 143, there is no problem in the case in which an orthodontic treatment is carried out by pressing a tooth. However, in the case in which a tooth that is recessed is pulled to a front in an orthodontic treatment, the arch wire 146 is broken out of the depressed part 145 that has been formed in the bracket 143 in some cases. Even in such a case, it is necessary that the arch wire 146 is tied up to the bracket 143 by using the wire 150 for a ligation.

Since it is necessary that the arch wire is tied up for the conventional orthodontic bracket as described above, the form of the conventional orthodontic bracket is complicated. Moreover, in the case in which a ligation is carried out, a tooth is prevented from being moved due to a ligation force in some cases. Moreover, the ligation operation is carried out by a hand work, and requires a high level of proficiency.

In the case in which a surface state and a shape of the orthodontic bracket becomes more complicated, food particles and debris remain in a gap that is formed by the orthodontic bracket, the arch wire, or the wire for a ligation in some cases. Such food particles and debris may cause a formation of the tooth decay in some cases.

An orthodontic treatment is carried out to improve a sensuousness of the teeth. In order to prevent the tooth decay in accordance with the above described orthodontic treatment from occurring and in consideration of an aesthetic property of the bracket and an operational property of a ligation, Japanese Patent Application Laid-Open Publication No. 2007-105361 (JP '361) discloses an invention of an orthodontic bracket in which a slot hole 252 that penetrates in a horizontal direction is formed in a base part 255 that is fixed on the surface of the teeth as shown in FIG. 12 herein. JP '361 discloses that the slot hole 252 is formed in such a manner that a penetrating direction of the slot hole 252 is different from a forming direction of the base part 255 and is inclined to the forming direction of the base part 255 in order to change an orthodontic treatment direction in accordance with each of the teeth as shown in FIG. 13. As described above, by displacing and inclining the slot hole 252 from the forming direction of the base part 255, a wiring direction of the arch wire is not linear, and a torque occurs by curving a wiring direction of the arch wire, thereby carrying out an orthodontic treatment of an angulation (an outward inclination) of the teeth.

However, there is one displaced slot hole 252 that is disclosed in JP '361. It is necessary that a torque for carrying out an orthodontic treatment of an outward inclination of the teeth depends on a torque that is caused by the elasticity of one arch wire that has been inserted into the slot hole 252. It is necessary that an arrangement of the entire teeth is corrected in a balanced manner for an orthodontic treatment. In the case in which a high torque is tried to be obtained in order to carry out an orthodontic treatment of an outward inclination of a part of the teeth, an extra stress is applied to other teeth.

The orthodontic bracket that is disclosed in JP '361 has a property in which food particles and debris are less likely to remain since a side surface of the orthodontic bracket is inclined. However, it is general that an adhesive agent is applied to the rear face of the orthodontic bracket above described, the side surface of the orthodontic bracket is picked up with tweezers, and the orthodontic bracket is mounted on the surface of the teeth. In the case in which the entire side surface is inclined as disclosed in JP '361 in the concrete, it is hard to pick up the orthodontic bracket with tweezers. Consequently, it is difficult that the orthodontic bracket that is disclosed in JP '361 is mounted on the surface of the teeth in an accurate fashion unfortunately.

Problems to be Solved by the Invention

An object of the present invention is to provide a new orthodontic bracket.

Moreover, an object of the present invention is to provide a new orthodontic bracket that can easily be mounted to the surface of the teeth in which food particles and debris are less likely to remain, whereby the orthodontic bracket does not cause the tooth decay to occur and a ligation that causes an operation property to be degraded is not required.

Moreover, an object of the present invention is to provide an orthodontic bracket in which a three-dimensional rotation force in which a central part of the bracket is the center of rotation can be applied to the teeth by mounting the bracket and a rotation stress can be easily adjusted.

Moreover, an object of the present invention is to provide an orthodontic bracket that has a high level of sensuousness by using a material having a color that is equivalent to that of the teeth and a high level of durability and an adhesive agent does not remain on the surface of the teeth in the case in which the bracket is detached.

SUMMARY OF THE INVENTION

An orthodontic bracket in accordance with the present invention is characterized by comprising a substrate surface that is bonded to a tooth surface and an arch wire retaining portion that is configured to retain an arch wire with the substrate surface as a bottom surface, the orthodontic bracket being connected by the arch wire and continuously applying a stress to individual teeth to thereby straighten a row of teeth, wherein the orthodontic bracket is in an approximately hog-backed cross sectional shape that is orthogonal to the direction in which the arch wire is stretched with the substrate surface bonded to the tooth surface as the bottom surface, and is provided with a plurality of arch wire through holes respectively for inserting the arch wire into the holes and connecting adjacent orthodontic brackets by the arch wire.

An orthodontic bracket in accordance with the present invention is characterized in that a cross sectional shape of the arch wire through hole is square-shaped preferably and at least three arch wire through holes are formed in the orthodontic bracket, whereby a more effective three-dimensional rotation torque can be applied to the teeth.

In particular, an orthodontic bracket in accordance with the present invention is characterized in that three arch wire through holes are formed in one bracket and a height from a virtual reference line that connects the both side end parts of the bracket in a cross section of the bracket for an arch wire through hole that is formed at the center is larger than that for arch wire through holes that are formed on the both sides. By the above configuration, the entire bracket can be smaller and in a smooth shape.

A shape of a cross section that is orthogonal to a stretching direction of the arch wire of the bracket is an approximately hog-backed shape. It is preferable that the shape is an approximately hog-backed shape in which $R_1$ where a center of a portion that is bonded to the cross section of a tooth is a virtual center is a radius, and there are at least four contact points, preferably at least six contact points, on a virtual semicircle that is on a flat surface that is equal to the cross section from the point of view of that food particles and debris are less likely to stick to the teeth.

The orthodontic bracket in accordance with the present invention is characterized in that a side that is bonded to a tooth surface is curved upward at a curvature of a radius $R_2$ from a virtual center that is virtualized below the bracket and on a flat surface that is equal to the cross section for the cross section of the bracket in order to retain an adhesive agent to bond the bracket to the tooth surface.

The orthodontic bracket in accordance with the present invention is characterized in that the arch wire through hole is inclined and formed in such a manner that a height of the both end parts of the through hole from the substrate surface is different from each other, whereby applying a rotation torque in a posterior-anterior direction of the teeth.

The orthodontic bracket in accordance with the present invention is characterized in that at least one adhesive agent filling groove that is parallel to the arch wire through hole is formed on the substrate surface that is bonded to a tooth surface of the bracket preferably.

The orthodontic bracket in accordance with the present invention is characterized in that a width in a gum direction of the bracket is smaller than a width in a direction of a tooth tip preferably.

The orthodontic bracket in accordance with the present invention is characterized in that an end part that is orthogonal to a stretching direction of the arch wire of the bracket is formed generally perpendicular to the substrate surface that is bonded to a tooth surface of the bracket preferably.

The orthodontic bracket in accordance with the present invention is characterized in that the bracket is made of a sintered object of an inorganic material.

An operation of a ligation is not required for the orthodontic bracket in accordance with the present invention. Consequently, the orthodontic bracket in accordance with the present invention is characterized in that the arch wire is fixed to the bracket by passing the arch wire through the arch wire through hole and the arch wire is not tied up to the orthodontic bracket by a ligation means.

In accordance with the present invention, an orthodontic bracket that is capable of performing a more effective three-dimensional motion and particularly an effective motion on the tooth surface can be provided. The orthodontic bracket in accordance with the present invention enables a more accurate orthodontic treatment. Moreover, since it is not necessary that the arch wire that has been disposed across the teeth is tied up to the orthodontic bracket, an orthodontic treatment can be carried out by applying a force smaller than a force that has been applied to the teeth with a conventional orthodontic bracket. Furthermore, since a shape of the orthodontic bracket in accordance with the present invention is simplified, a deposition of a bacterial plaque (food residue) can be less to the bracket. Consequently, the orthodontic bracket in accordance with the present invention is excellent in terms of an oral hygiene.

Moreover, the orthodontic bracket in accordance with the present invention is provided with a color tone similar to that of the tooth surface in essence, is hard, and has a high level of sensuousness and a high level of durability.

Moreover, the orthodontic bracket in accordance with the present invention is provided with an excellent adhesive property to the tooth surface. An adhesive agent can be prevented from remaining on the tooth surface in the case in which the orthodontic bracket is detached. All the adhesive agent is retained on the rear surface (substrate surface) of the orthodontic bracket that is to be removed and then the adhesive agent is eliminated.

DETAILED DESCRIPTION OF THE INVENTION

An orthodontic bracket in accordance with the present invention will be described below in detail with reference to the drawings.

Figure 1:
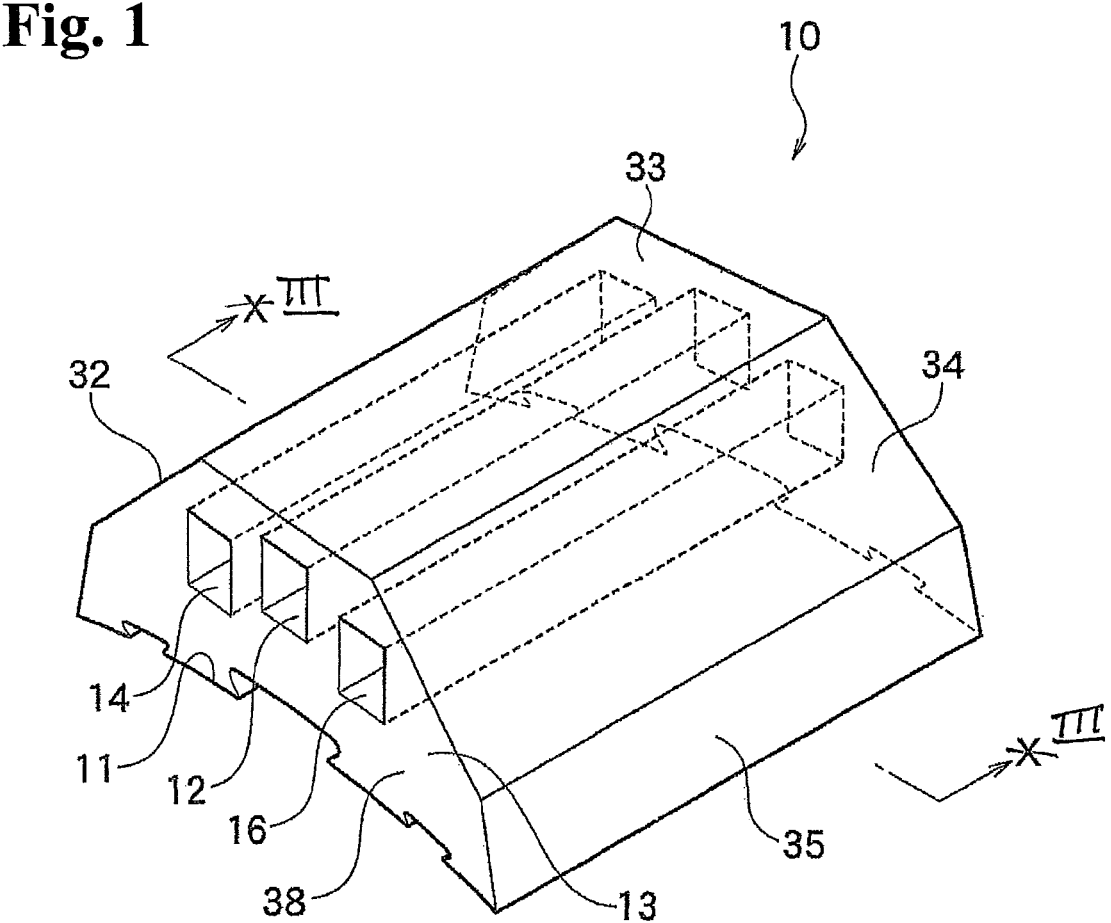
FIG. 1 is a perspective view showing an orthodontic bracket in accordance with an embodiment of the present invention.
Figure 3:
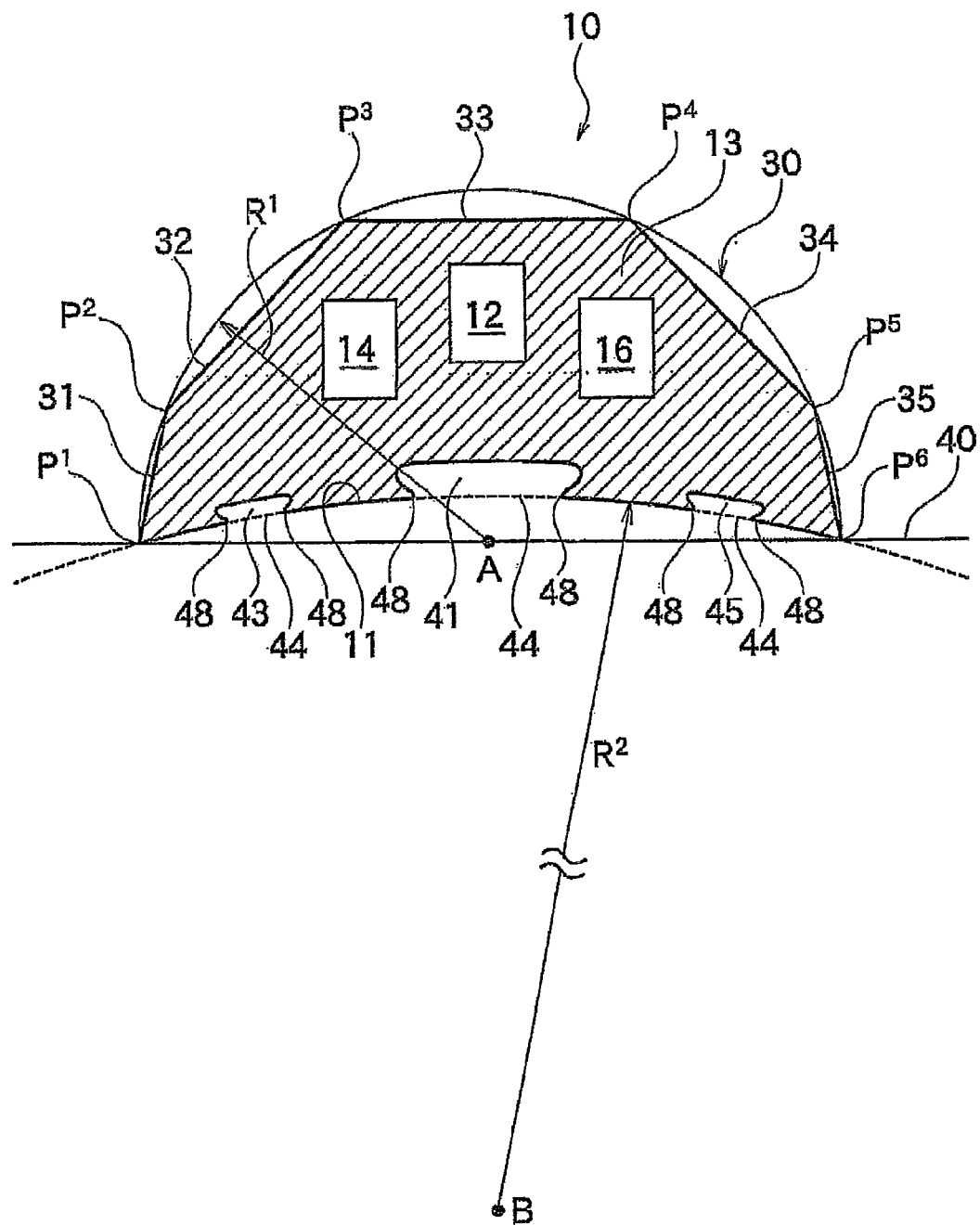
FIG. 3 is a cross-sectional view taken along the line of an orthodontic bracket in accordance with an embodiment of the present invention shown in FIG. 1.

As shown in FIG. 1, an orthodontic bracket 10 in accordance with the present invention is comprised of a substrate surface 11 that is bonded to a tooth surface and an arch wire retaining portion 13 that is provided with a plurality of through holes that are configured to retain an arch wire (see FIG. 3 too). Unlike a conventional bracket, for the orthodontic bracket 10 in accordance with the present invention, an arch wire is not exposed and is inserted and stretched into a plurality of through holes that have been formed in the orthodontic bracket 10. FIG. 1 shows a mode in which three through holes are formed. However, at least two through holes can be formed in the present invention. It is preferable that a through hole 14 and a through hole 16 are symmetrically disposed to right and left from a through hole 12 as a center as shown in FIG. 1 in order to apply a three-dimensional stress to the teeth that are to be corrected in the case of an orthodontic treatment.

Figure 2A:
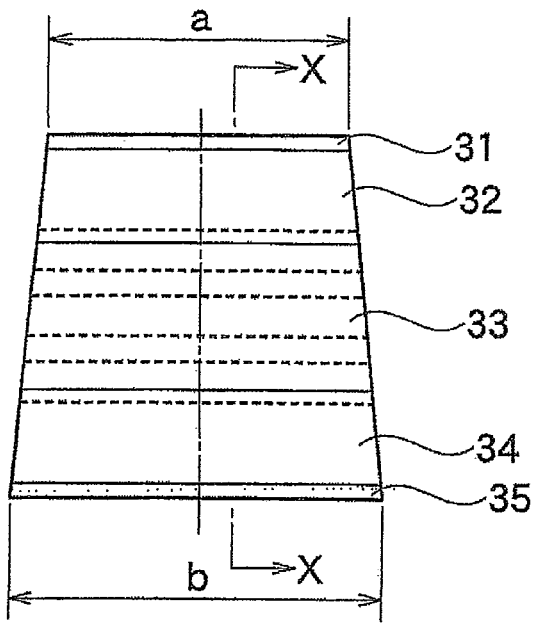
FIG. 2A is a top view showing an orthodontic bracket in accordance with an embodiment of the present invention, respectively.
Figure 2B:
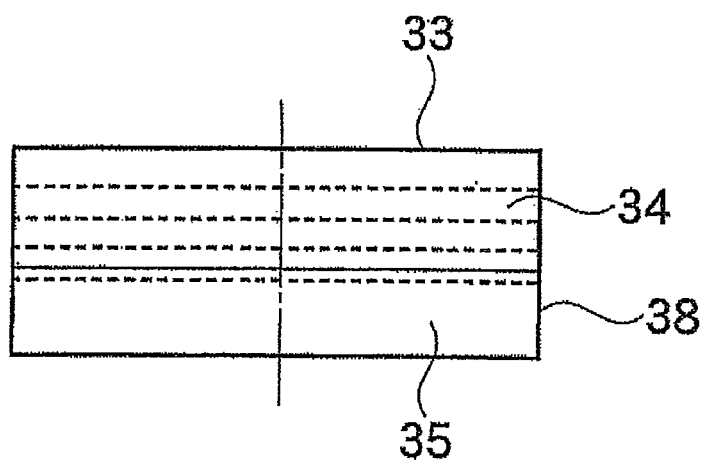
FIG. 2B is a side view, and a rear face view showing an orthodontic bracket in accordance with an embodiment of the present invention, respectively.
Figure 2C:
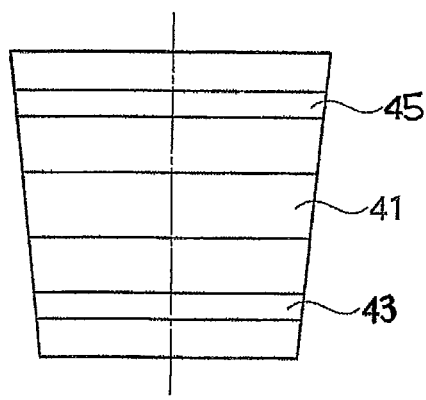
FIG. 2C is a rear face view showing an orthodontic bracket in accordance with an embodiment of the present invention, respectively.

The orthodontic bracket 10 in accordance with the present invention is in an approximately hog-backed shape as shown in FIG. 1. As clarified in detail by a perspective view shown in FIG. 1, a top view shown in FIG. 2(a), a side view shown in FIG. 2(b), and a rear face view shown in FIG. 2(c), the orthodontic bracket 10 is in an approximately hog-backed shape in which a width a in a gum direction of the bracket is slightly smaller than a width b in a direction of a tooth tip. As clarified by FIG. 1 and FIG. 2(a), a shape of the top surface of the orthodontic bracket 10 in accordance with the present invention is not one circular arc to be precise, but a plurality of planes or circular arcs are connected to form an approximately hog-backed shape as a whole. FIG. 3 is an expanded cross-sectional view taken along the line III-III of the orthodontic bracket shown in FIG. 1 and FIG. 2(a) (a cross-sectional shape that is orthogonal to the direction in which the arch wire is stretched with the substrate surface bonded to the tooth surface as the bottom surface).

As clarified by FIG. 3, the orthodontic bracket 10 in accordance with the present invention is in an angular hog-backed shape in which flat plates 31, 32, 33, 34, and 35 are connected in such a manner that at least four points, preferably six points $P^1$, $P^2$, $P^3$, $P^4$, $P^5$, and $P^6$ come into contact with a virtual circular arc 30 of a radius $R_1$ from a virtual center A as a center with a center of a portion that is bonded to a cross section of the teeth as the virtual center A for the cross section of the orthodontic bracket 10. Although it is not shown, it is preferable that the contact parts of the flat plates 31, 32, 33, 34, and 35 are chamfered to make the angular hog-backed shape to be similar to a semicircular hog-backed shape. As a matter of course, an outer peripheral surface of the orthodontic bracket in accordance with the present invention can be equivalent to the virtual circular arc 30 of a radius $R_1$. In the present invention, the radius $R_1$ for forming the virtual circular arc 30 can be selected arbitrarily in accordance with a size of the teeth on which the orthodontic bracket 10 is mounted. However, the radius $R_1$ is in the range of 2 to 3 mm in terms of a size of the general teeth by ordinary.

By forming the orthodontic bracket 10 in accordance with the present invention in a hog-backed shape that is approximate to the virtual circular arc 30 as described above, food particles and debris are less likely to remain on the orthodontic bracket 10 and a sensuousness of the orthodontic bracket 10 can be improved.

As shown in FIG. 1 and FIG. 3, a plurality of through holes is formed in the orthodontic bracket in accordance with the present invention. It is necessary that at least two through holes are formed, and it is preferable that at least three through holes are formed. However, it is extremely difficult in manufacturing that more than four through holes are formed. Even in the case in which more than three through holes are formed, an advantageous effect for an orthodontic treatment is not improved.

Consequently, it is preferable that the number of through holes that are formed in the orthodontic bracket 10 in accordance with the present invention is three in particular. The through holes are formed in such a manner that the through holes are disposed across between the both end parts 38 and 38 of the orthodontic bracket 10 in accordance with the present invention. The plurality of through holes is linear and is formed parallel to the direction in which the arch wire is stretched in essence.

Figure 4:
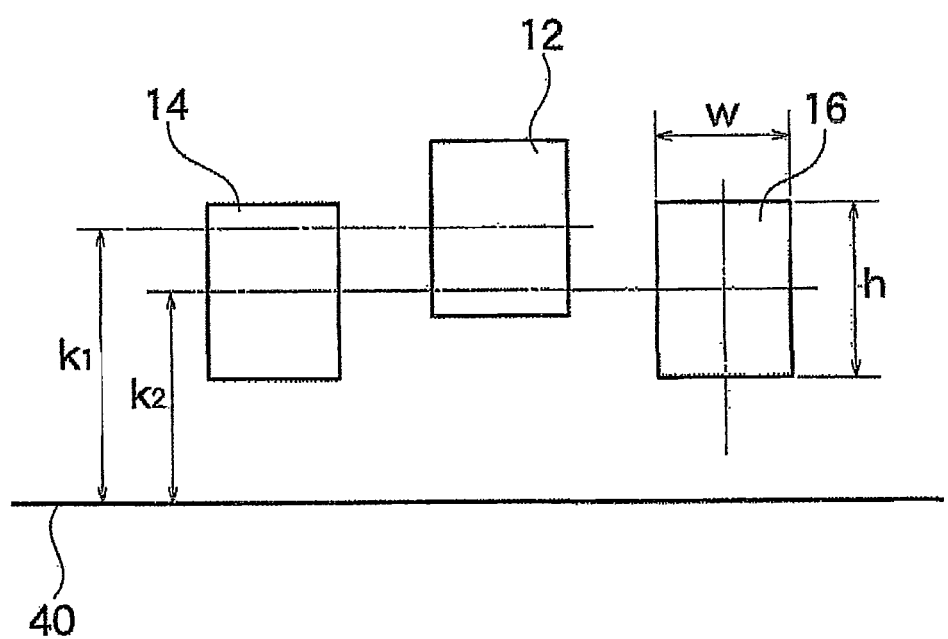
FIG. 4 is a view schematically showing a location relationship of a plurality of through holes that are formed in the orthodontic bracket in accordance with an embodiment of the present invention.

FIGS. 1, 3, and 4 show the through holes 12, 14, and 16 that are provided with a square cross sectional shape. However, the cross sectional shape of the through holes 12, 14, and 16 is not restricted to a square shape, and can also be a mode such as a circular shape, a polygonal shape, and a trapezoid shape. However, in the case in which a directional property is tried to be generated to a stress that is applied to the teeth by using an arch wire that is provided with a square cross sectional shape, a directional property can be generated more easily advantageously by making a cross sectional shape of the through holes 12, 14, and 16 to be square-shaped.

Figure 7:
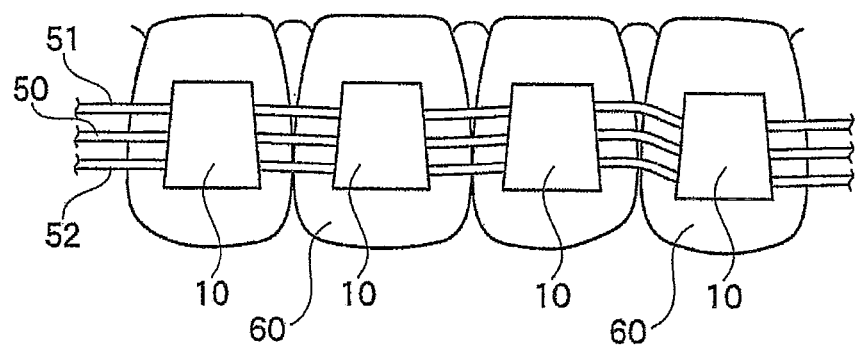
FIG. 7 is a schematic view showing an example of a usage mode of an orthodontic bracket in accordance with an embodiment of the present invention, in which the orthodontic bracket is bonded to the surface of the teeth and an arch wire passes through the orthodontic bracket.

An embodiment in which three through holes are formed will be described as an example. As shown in FIGS. 3 and 4, a center point of the through hole 12 that is located at the center is disposed 1.0 to 2.0 mm by ordinary, 1.2 to 1.7 mm preferably above a virtual reference line 40 (that is, $k_1$ is in the range of 1.0 to 2.0 mm by ordinary, 1.2 to 1.7 mm preferably in FIG. 4), and a height of a center point of the through holes 14 and 16 that are located on the sides of the through hole 12 from the virtual reference line 40 is in the range of 0.8 to 1.8 mm by ordinary, 1.0 to 1.5 mm preferably (that is, $k_2$ is in the range of 0.8 to 1.8 mm by ordinary, 1.0 to 1.5 mm preferably in FIG. 4). Consequently, the through hole 12 that is located at the center is disposed on the upper side from the virtual reference line 40 by ¼ to ¾ of a height h of the through hole as compared with the through holes 14 and 16 that are located on the sides of the through hole 12. A location of the through hole 12 that is located at the center is made higher as described above, a main arch wire is inserted into the through hole 12, and a diameter and a tension of an arch wire that is inserted into the through holes 14 and 16 are adjusted in consideration of the arch wire that is inserted into the through hole 12. By this configuration, a three-dimensional torque or stress can be applied to the teeth. In particular, by the adjustment of the tension, a torque or stress that is effective to an orthodontic treatment can be applied in the case in which a tooth is grown at an angle from a gum when the teeth are viewed from a front side (for instance, when the teeth are viewed as shown in FIG. 7). In addition, the entire orthodontic bracket can be smaller and in a smooth shape, whereby food particles and debris are less likely to stick to the orthodontic bracket and the teeth.

Figure 8:
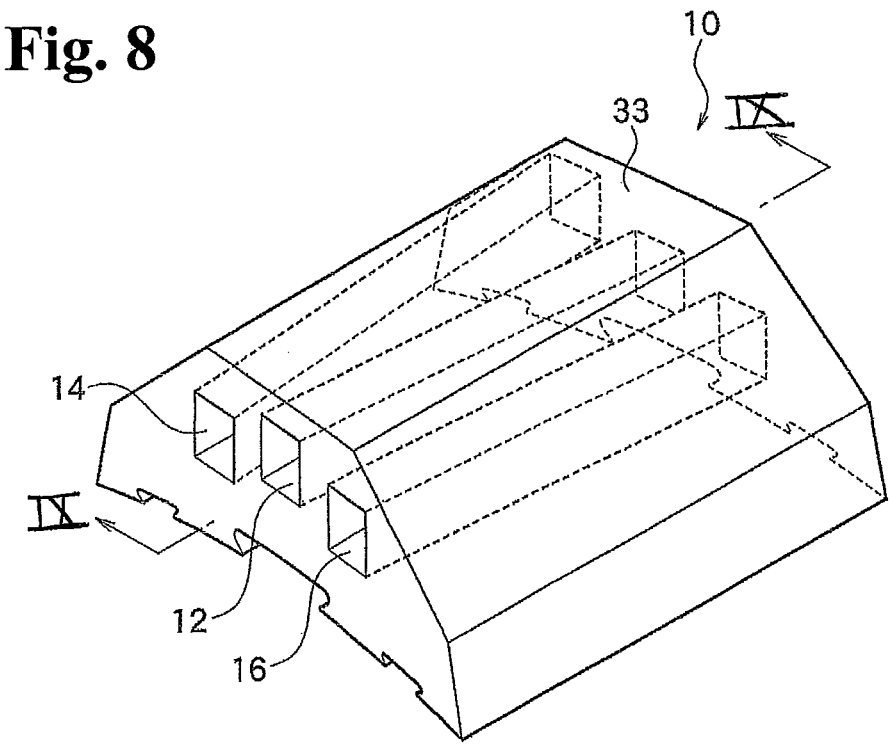
FIG. 8 is a perspective view showing a mode of an arch wire through hole of an orthodontic bracket in accordance with an embodiment of the present invention in which the arch wire through hole is inclined and formed in such a manner that a height of the both end parts of the through hole from the substrate surface of the bracket (or a tooth surface) is different from each other.
Figure 9:
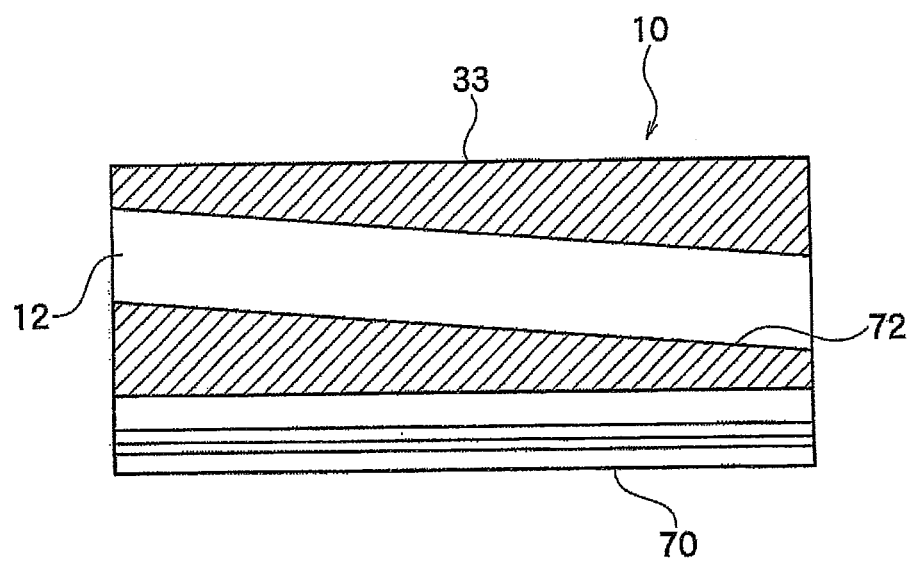
FIG. 9 is a cross-sectional view taken along the line IX-IX of an orthodontic bracket in accordance with an embodiment of the present invention shown in FIG. 8.
Figure 10:
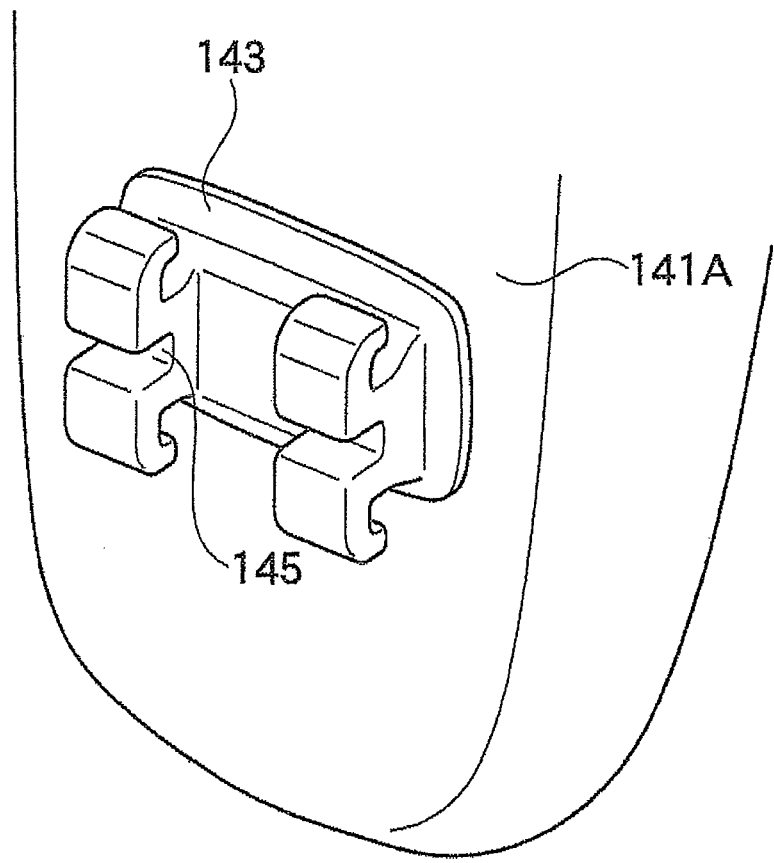
FIG. 10 is a perspective view showing a conventional orthodontic bracket.
Figure 11:
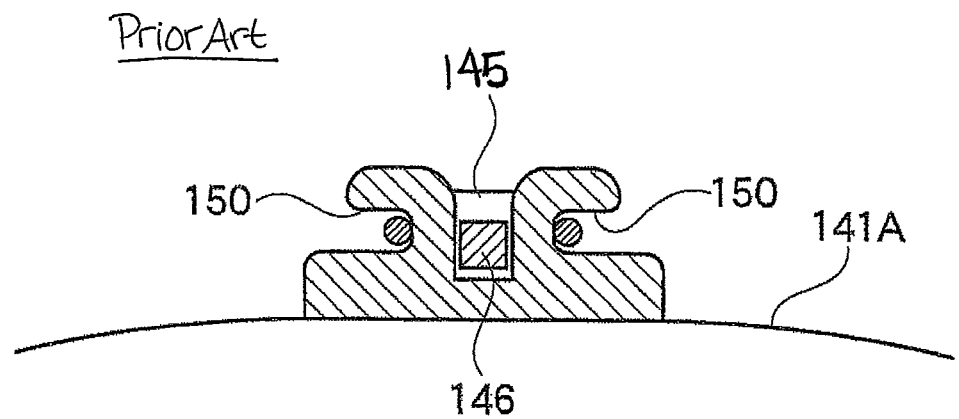
FIG. 11 is a cross-sectional view showing a state in which an arch wire is tied up by using the bracket shown in FIG. 10.
Figure 12:
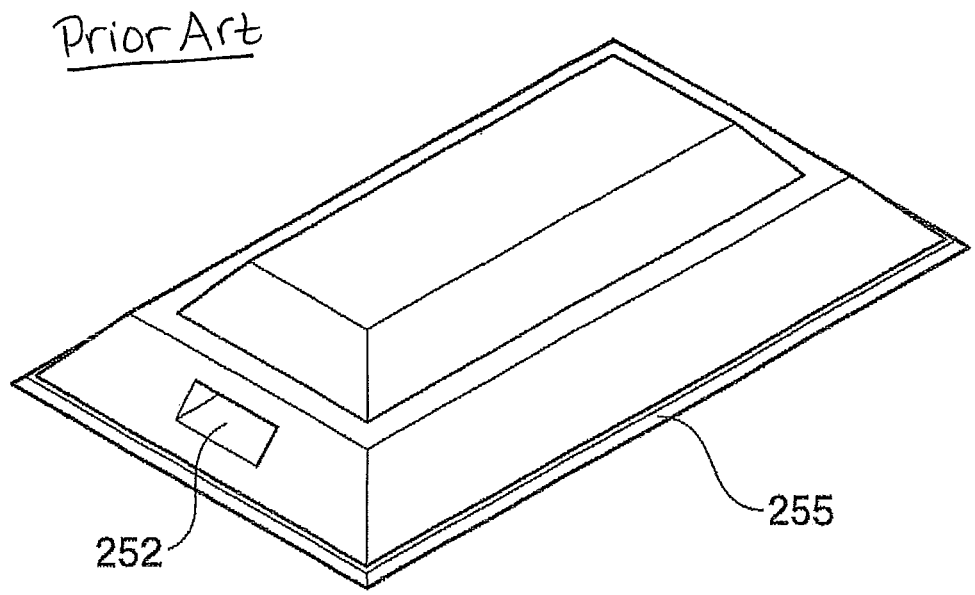
FIG. 12 is a perspective view showing another mode of a conventional orthodontic bracket.
Figure 13:
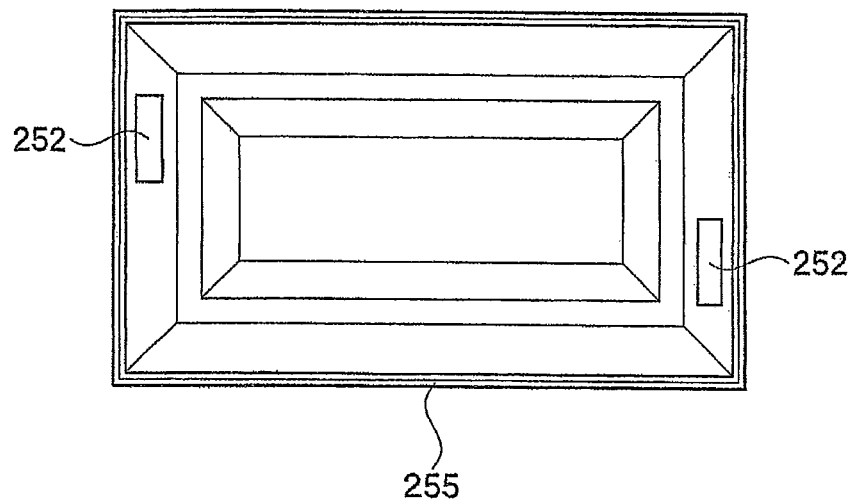
FIG. 13 is a plan view showing the mode of the conventional orthodontic bracket shown in FIG. 12, in which a penetrating direction of a slot hole is inclined to the forming direction of the base part in such a manner that a penetrating direction of a slot hole is varied from a forming direction of a base part.

As shown in FIG. 8 moreover, for the orthodontic bracket in accordance with the present invention, the arch wire through holes 12, 14 and 16 can also be formed at an angle in such a manner that the heights of the both end parts of the through hole from a substrate surface (or a tooth surface) are different from each other. In other words, the arch wire through holes 12, 14 and 16 can also be formed not parallel to the substrate surface or the tooth surface. In other words moreover, the arch wire through holes 12, 14 and 16 can also be formed in such a manner that in the case in which a parallel displacement of the arch wire through holes 12, 14 and 16 is carried out downward (to the substrate surface side) and the end part of the arch wire through hole comes into contact with the substrate surface or the tooth surface for the first time, the arch wire through hole and the substrate surface or the tooth surface take the form of an acute angle. FIG. 9 is a cross-sectional view of the arch wire through hole 12 that has been formed in such a manner that the arch wire through hole 12 is inclined as described above. In FIG. 9, a straight line 72 of the lower side of the arch wire through hole 12 and a straight line 70 that represents the substrate surface or the tooth surface take the form of an acute angle.

As described above, an arch wire is inserted into the arch wire through hole 12, 14 or 16 that has been formed in such a manner that a distance of one end part of the through hole from the tooth surface is different from a distance of the other end part of the through hole from the tooth surface, and a tension is applied to the arch wire. By this configuration, a three-dimensional torque or stress can be applied to the teeth in a posterior-anterior direction, whereby the prominent teeth can be corrected for instance.

Although a plurality of arch wire through holes are formed for the orthodontic bracket in accordance with the present invention, a state of an inclination of the plurality of arch wire through holes (an acute angle that is formed in the case in which a parallel displacement of the arch wire through holes is carried out and the end part of the arch wire through hole comes into contact with the substrate surface or the tooth surface) can be equivalent to each other or can be different from each other. In the case in which a state of an inclination is equivalent to each other, a torque in a posterior-anterior direction can be applied to the teeth with uniformity. On the other hand, in the case in which a state of an inclination is different from each other, a torque in a posterior-anterior direction is different depending on a location of a tooth and a complex torque can be applied.

Although a size of the through hole is different depending on an arch wire that is used, a height h of the through hole is in the range of 0.5 to 0.8 mm and a width w is in the range of 0.5 to 0.7 mm under normal conditions. Even in the case in which a shape of the through hole is modified, a size of the through hole can be selected with reference to the above size.

The virtual reference line 40 that has been adopted in the above descriptions is a virtual line that is corresponded to a surface which the points $P^1$ and $P^6$ that are the both side end parts come into contact with (a line that is virtualized with the both side end parts connected) in the case in which the orthodontic bracket is disposed on the flat surface as shown in FIG. 3.

Figure 5:
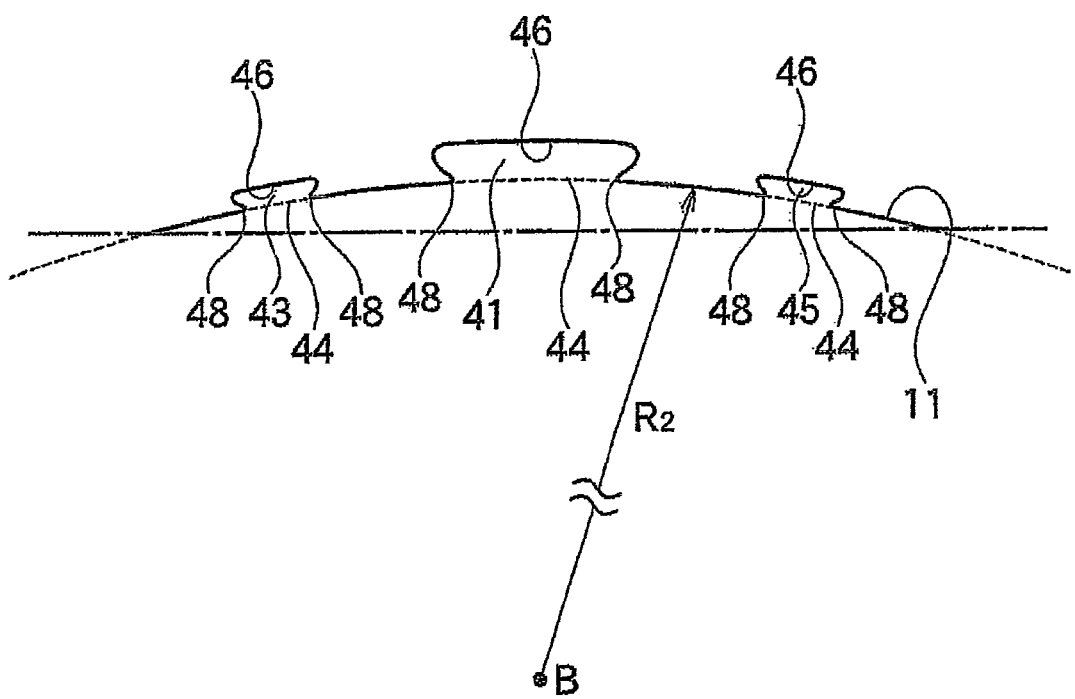
FIG. 5 is a schematic view showing an example of depressions for an adhesive agent that are formed on the substrate surface of the orthodontic bracket in accordance with an embodiment of the present invention.

On the substrate surface that is bonded to the tooth surface for the orthodontic bracket in accordance with the present invention, at least one adhesive agent filling groove that is configured to hold an adhesive agent is formed to bond the bracket to the tooth surface. In FIGS. 2, 3, and 5, three adhesive agent filling grooves 41, 43, and 45 are formed on the substrate surface 11 of the orthodontic bracket in accordance with the present invention. It is preferable that an overhang 48 is formed toward the inside of an opening part 44 on a peripheral part of the opening part 44 for the adhesive agent filling grooves 41, 43, and 45. By this configuration, it is preferable that the adhesive agent filling grooves 41, 43, and 45 are formed in such a manner that a space of the opening part 44 is smaller than a bottom part 46 of the adhesive agent filling groove for the adhesive agent filling grooves 41, 43, and 45. The adhesive agent filling grooves 41, 43, and 45 are filled with a slightly excess adhesive agent. The substrate surface 11 of the orthodontic bracket in accordance with the present invention is not flat. A side that is bonded to a tooth surface is curved upward in an arch shape at a curvature of a radius $R_2$ from a virtual center B that is virtualized below the bracket and on a flat surface that is equal to the cross section for the cross section that is orthogonal to the direction in which the arch wire is stretched with the substrate surface 11 that is bonded to the tooth surface as the bottom surface for the bracket. This is because the tooth surface is not formed in a straight line pattern and a space in which an adhesive agent is extended is formed to bond the bracket to the tooth surface. In this case, the radius $R_2$ is in the range of 5 to 20 mm by ordinary, 10 to 15 mm preferably.

Since an arch wire is inserted into the arch wire through holes 12, 14 and 16 that have been formed in the bracket for the orthodontic bracket in accordance with the present invention as described above, the arch wire is fixed by an inner peripheral wall surface of the arch wire through holes 12, 14 and 16. Consequently, unlike the conventional configuration, it is not necessary that the arch wire is tied up.

In the case in which the orthodontic bracket in accordance with the present invention is bonded to a tooth surface, the adhesive agent filling grooves 41, 43, and 45 are filled with a slightly much adhesive agent, and the bracket is then pressed to the tooth surface in such a manner that the adhesive agent is spread to the entire rear face of the bracket. By pressing the bracket to the tooth surface, an adhesive agent that has been filled slightly excessively in the adhesive agent filling grooves is supplied to a space between the teeth and the rear face of the orthodontic bracket that has been formed in an arc shape, and the adhesive agent bonds the bracket to the teeth strongly. The overhang 48 that is formed toward an inner ringside of an opening part has an anchor effect that operates in such a manner that an adhesive agent that is disposed in the adhesive agent filling grooves 41, 43, and 45 is not dropped out.

On the other hand, in the case in which the orthodontic bracket in accordance with the present invention is removed, an adhesive strength of the adhesive agent to the tooth surface is decreased and the orthodontic bracket is removed. In this case, an anchor effect of the overhang 48 enables the adhesive agent not to remain on the tooth surface and the adhesive agent is removed together with the orthodontic bracket. Consequently, an adhesive agent hardly remains on the tooth surface.

As described above, the adhesive agent filling grooves 41, 43, and 45 that has been formed on a substrate surface side of the orthodontic bracket in accordance with the present invention are filled with a slightly excess adhesive agent as compared with an amount that can be held, the orthodontic bracket is pressed to the tooth surface, and a gap between the orthodontic bracket and the tooth surface is also filled with the adhesive agent, whereby the orthodontic bracket is bonded to the tooth surface. As an adhesive agent that is used here, a general adhesive agent that is used for adhesive bonding of the orthodontic bracket and that is not harmful to a human body can be used.

After the orthodontic bracket in accordance with the present invention is bonded to a surface of each tooth as described above, an arch wire is inserted into the arch wire through holes that have been formed in the orthodontic bracket in accordance with the present invention, and each orthodontic bracket is connected by using the arch wire that has been inserted into the arch wire through holes.

A plurality of through holes, preferably three through holes, is formed in the orthodontic bracket in accordance with the present invention. After the main arch wire 50 is inserted into the arch wire through hole 12 that is located at the center, the arch wires 51 and 52 are inserted into the arch wire through holes 14 and 16 that are located on the sides of the arch wire through hole 12 as needed (see FIG. 7).

In this configuration, the main arch wire 50, the arch wire 51, and the arch wire 52 can be equivalent to each other or can be different from each other.

Moreover, in the case in which a direction of applying a tension to the arch wire 51 and a direction of applying a tension to the arch wire 52 are made to be in reverse from the main arch wire 50 as a center, a higher rotation torque can be applied to the teeth. For instance, in the case in which a wire that is provided with a stiffness property higher than that of the arch wire 51 and the arch wire 52 is used as the main arch wire 50, a stress for setting in motion in a posterior-anterior direction can be applied to the teeth by the main arch wire 50. Moreover, in the case in which a direction of applying a tension to the arch wire 51 and a direction of applying a tension to the arch wire 52 are made to be in reverse, a rotation torque can be applied to the teeth. More specifically, a three-dimensional orthodontic treatment can be carried out by modifying the characteristics or a direction of a tension of the three wires as described above.

Moreover, the arch wire through holes can also be formed at an angle in such a manner that the heights of the both end parts of the through hole from a substrate surface of the orthodontic bracket in accordance with the present invention (or a tooth surface) are different from each other as described above. In the case in which a tension is applied to the arch wire that has been inserted into the arch wire through hole that has been formed as described above, a torque or a stress for setting in motion in a posterior-anterior direction can be applied to the teeth more effectively.

In particular, a rotation torque that is applied to the teeth can be controlled with freedom by adjusting the arch wire 51 and the arch wire 52. Moreover, an orthodontic treatment in a posterior-anterior direction can be carried out at a preferable strength by adjusting the main arch wire 50 and by adjusting an inclination of the arch wire through hole. Consequently, an orthodontic treatment can be carried out for the orthodontic bracket in accordance with the present invention while an inflammatory disorder caused by a contact of adjacent roots of the teeth and a necrosis of a root of a tooth can be prevented from occurring in an effective manner.

The orthodontic bracket in accordance with the present invention can be manufactured by sintering an inorganic material. In particular, in the case in which a zirconium oxide is put in a mold and is sintered after a jig for forming a through hole is mounted, a through hole can be formed with a high accuracy for a densification. Moreover, since a color tone of an orthodontic bracket that has been formed by using a zirconium oxide as described above is similar to a color tone of the teeth, the orthodontic bracket is extremely aesthetic. Furthermore, since a sintered object of a zirconium oxide is provided with an extremely high strength, an orthodontic bracket can be prevented from being damaged in an orthodontic treatment.

Moreover, it is not necessary that a special bracket is prepared to correct an angulation of the teeth. Only one type of a bracket enables an angulation of the teeth to be corrected. Furthermore, it is not necessary that a bonding direction of a bracket is modified to correct an angulation of the teeth. The bracket can be bonded along a center line of a tooth 60 that has been grown from a gum 65, and it is not necessary that the bracket is bonded at an angle in consideration of a state of the teeth (see FIG. 7).

Figure 6:
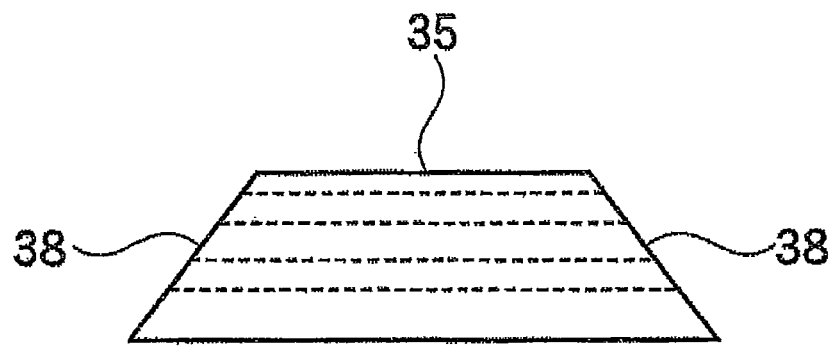
FIG. 6 is a side view showing another mode of an orthodontic bracket in accordance with an embodiment of the present invention.

In the above descriptions, an embodiment in which the both end parts of the orthodontic bracket is cut up vertically as shown in FIG. 2(*b*) has been used mainly. This is because it is necessary that the bracket is picked up with tweezers in the case in which the bracket is mounted. In the case in which the both end parts are tapered, it is hard to pick up the bracket. However, in the case in which the vacuum tweezers or a bonding jig with removability is used as substitute for the tweezers, it is not necessary that the both end parts of the orthodontic bracket is cut up vertically in particular, and the both side faces can be tapered as shown in FIG. 6 for instance.

The orthodontic bracket in accordance with the present invention is not restricted to the above embodiments, and various changes, modifications, and functional additions can be thus made without departing from the scope and purpose of the present invention.

Since it is not necessary that the arch wire is tied up for the orthodontic bracket in accordance with the present invention, an orthodontic bracket can be easily mounted on the tooth surface. Moreover, food particles and debris are less likely to remain, whereby the orthodontic bracket does not cause the tooth decay to occur.

Moreover, the orthodontic bracket in accordance with the present invention is provided with a plurality of through holes, and a plurality of arch wires can be stretched in the through holes. Consequently, a three-dimensional orthodontic treatment for setting in motion in a posterior-anterior direction to the teeth can be carried while a rotation torque is applied to the teeth by controlling a type of an arch wire, a tension to be applied, and an inclination of a through hole.

The orthodontic bracket in accordance with the present invention is made of a sintered object of a metal oxide, preferably a sintered object of a zirconium oxide. Consequently, the orthodontic bracket has a high level of sensuousness and a high level of durability.

For the orthodontic bracket in accordance with the present invention, the totally gradual depressed part is formed on the bonded surface between the orthodontic bracket and the teeth, and an adhesive agent filling groove of a depressed shape is formed on the orthodontic bracket. Since an opening part of the adhesive agent filling groove is provided with an shape overhanging to the inside part of the opening part, the orthodontic bracket that has been bonded is not dropped out of the teeth. Moreover, in the case in which the orthodontic bracket is detached, an adhesive agent does not remain on the tooth surface, and an adhesive agent can be removed together with the orthodontic bracket.

Furthermore, the orthodontic bracket in accordance with the present invention enables a variety of three-dimensional motions to be applied. By this configuration, it is expected that more effective and more accurate orthodontic treatment can be carried out.

The invention claimed is:

1. An orthodontic bracket comprising: a substrate surface configured to be bonded to a tooth surface; and, an arch wire retaining portion that is configured to retain an arch wire,
   the orthodontic bracket being configured to connect to the arch wire and to continuously apply a stress to individual teeth to thereby straighten a row of teeth,
   wherein a cross section of the bracket that is orthogonal to a direction in which the arch wire is stretched, with the substrate surface bonded to the tooth surface as a bottom edge, is an approximately cambered shape, in which the bracket cross section is shaped to have a circumscribed first virtual semicircle, the first virtual semicircle having a radius $R_1$ and a virtual center positioned at a center of the bottom edge of the cross section, the first virtual semicircle contacting at least four contact points on the cross section of the bracket,
   wherein the orthodontic bracket includes flat plates, the flat plates being arranged such that the cross section of the bracket comprises straight lines defined by an edge of one of the flat plates, the straight lines connecting adjacent contact points of the bracket cross section,
   wherein the orthodontic bracket is provided with a plurality of arch wire through holes respectively for inserting the arch wire into the arch wire through holes and connecting adjacent orthodontic brackets by the arch wire,
   wherein the orthodontic bracket is an integrated object formed by inputting a bracket formation material into a mold and attaching a jig for forming the through holes, thereby forming the bracket in the desired shape,
   wherein the substrate surface comprises a curved surface such that the bottom edge of the cross section of the bracket defines a second virtual semicircle having a radius $R_2$ that is different than the radius $R_1$ of the first virtual semicircle, and
   wherein the curved surface comprises at least one adhesive agent filling dovetail groove arranged such that a width of an opening of the dovetail groove is smaller than a width of an interior of the dovetail groove.

2. The orthodontic bracket as defined in claim 1, wherein a cross sectional shape of one of the plurality of arch wire through holes is square-shaped and the plurality of arch wire through holes comprises at least three arch wire through holes are formed in the orthodontic bracket.

3. The orthodontic bracket as defined in claim 1, wherein the plurality of arch wire through holes includes a center arch wire through hole positioned between two side arch wire through holes and wherein the center through hole is positioned a distance farther from the substrate surface than the distance from the substrate surface to the two side through holes.

4. The orthodontic bracket as defined in claim 1, wherein the cross section of the bracket is shaped such that the first virtual semicircle contacts six points on the cross section of the bracket.

5. The orthodontic bracket as defined in claim 4, wherein the second virtual center is virtualized below the bracket and on a flat surface that is coplanar with the cross section of the bracket.

6. The orthodontic bracket as defined in claim 1, wherein at least one of the plurality of arch wire through holes is inclined and formed in such a manner that a height of both end parts of said at least one of the plurality of arch wire through holes from the substrate surface is different from each other.

7. The orthodontic bracket as defined in claim 1, wherein at least one of the at least one adhesive agent filling dovetail grooves is parallel to at least one of the plurality of arch wire through holes.

8. The orthodontic bracket as defined in claim 1, wherein a width in an apical direction of the bracket is smaller than a width in a coronal direction of the bracket.

9. The orthodontic bracket as defined in claim 1, wherein an end part that is orthogonal to a stretching direction of the arch wire of the bracket is formed perpendicular to the substrate surface that is bonded to a tooth surface of the bracket.

10. The orthodontic bracket as defined in claim 1, wherein the bracket is made of a sintered object of an inorganic material.

11. The orthodontic bracket as defined in claim 1, wherein the bracket is configured such that when the arch wire is passed through one of the plurality of arch wire through holes, the arch wire is fixed by an inner peripheral wall surface of said one of the plurality of arch wire through holes.

12. The orthodontic bracket as defined in claim 2, wherein the plurality of arch wire through holes includes a center arch wire through hole positioned between two side arch wire through holes and, wherein the center arch wire through hole is positioned a distance farther from the substrate surface than the distance from the substrate surface to the two side arch wire through holes.

13. An assembly comprising:
   the orthodontic bracket as defined in claim 1; and
   an adhesive agent configured to bond the orthodontic bracket to the tooth surface, the adhesive agent being at least partially disposed within the at least one adhesive agent filling dovetail groove.

14. The orthodontic bracket as defined in claim 1, wherein each of the plurality of arch wire through holes is entirely enclosed in a longitudinal direction by the orthodontic bracket.

* * * * *